US012747379B2

(12) United States Patent
Fujita et al.

(10) Patent No.: US 12,747,379 B2
(45) Date of Patent: Sep. 29, 2026

(54) COMPOUND AND POLYMER COMPOSITION INCLUDING SAID COMPOUND

(71) Applicant: Mitsubishi Chemical Corporation, Tokyo (JP)

(72) Inventors: Kanami Fujita, Tokyo (JP); Mitsunori Sugihara, Tokyo (JP)

(73) Assignee: Mitsubishi Chemical Corporation, Tokyo (JP)

( * ) Notice: Subject to any disclaimer, the term of this patent is extended or adjusted under 35 U.S.C. 154(b) by 978 days.

(21) Appl. No.: 17/946,348

(22) Filed: Sep. 16, 2022

(65) Prior Publication Data

US 2023/0022690 A1 Jan. 26, 2023

Related U.S. Application Data

(63) Continuation of application No. PCT/JP2021/010798, filed on Mar. 17, 2021.

(30) Foreign Application Priority Data

Mar. 24, 2020 (JP) ................................ 2020-053216

(51) Int. Cl.

| | |
|---|---|
| ***C09J 133/08*** | (2006.01) |
| ***C07C 69/593*** | (2006.01) |
| ***C08F 220/18*** | (2006.01) |
| ***C08F 290/04*** | (2006.01) |
| ***C09J 7/10*** | (2018.01) |
| ***C09J 133/14*** | (2006.01) |

(52) U.S. Cl.

CPC .......... *C09J 133/08* (2013.01); *C07C 69/593* (2013.01); *C08F 220/1804* (2020.02); *C08F 290/04* (2013.01); *C09J 7/10* (2018.01); *C09J 133/14* (2013.01); *C09J 2433/00* (2013.01)

(58) Field of Classification Search

CPC ...... C09J 133/04; C09J 133/14; C08F 290/02; C08F 290/04; C08F 290/046; C08L 33/04; C08L 33/14

See application file for complete search history.

(56) References Cited

U.S. PATENT DOCUMENTS

| | | | | |
|---|---|---|---|---|
| 2008/0032221 | A1 * | 2/2008 | Lin | G03G 5/144 430/58.65 |
| 2011/0063567 | A1 | 3/2011 | Domschke et al. | |
| 2014/0302313 | A1 | 10/2014 | Suwa et al. | |
| 2016/0168298 | A1 | 6/2016 | Woods et al. | |
| 2019/0276717 | A1 | 9/2019 | Masuda et al. | |
| 2020/0010697 | A1 * | 1/2020 | Taniguchi | C08F 230/085 |
| 2020/0216724 | A1 | 7/2020 | Lee et al. | |

FOREIGN PATENT DOCUMENTS

| | | | | |
|---|---|---|---|---|
| CN | 102498431 | A | 6/2012 | |
| CN | 113302217 | A | 8/2021 | |
| EP | 3901188 | A1 | 10/2021 | |
| JP | H10-168408 | A | 6/1998 | |
| JP | 2004-182924 | A | 7/2004 | |
| JP | 2008-169307 | A | 7/2008 | |
| JP | 2013-040256 | A | 2/2013 | |
| JP | 2013-504682 | A | 2/2013 | |
| JP | 2017-066294 | A | 4/2017 | |
| JP | 2018-504509 | A | 2/2018 | |
| JP | 2019-199578 | A | 11/2019 | |
| KR | 10-2017-0115227 | A | 10/2017 | |
| WO | 2015/155844 | A1 | 10/2015 | |
| WO | WO-2018181668 | A1 * | 10/2018 | C09D 7/20 |
| WO | 2019/066528 | A1 | 4/2019 | |
| WO | 2020/158475 | A1 | 8/2020 | |

OTHER PUBLICATIONS

Office Action issued in corresponding Japanese Patent Application No. 2022-510003 dated Jan. 14, 2025.

Office Action issued Mar. 1, 2024 for Chinese Patent Application No. 202180016178.3.

Office Action issued in corresponding Taiwan Patent Application No. 110110052 dated Jul. 29, 2024.

Office Action issued in corresponding Japanese Patent Application No. 2022-510003 dated Sep. 17, 2024.

Decision of Rejection issued May 14, 2024 for Chinese Patent Application No. 202180016178.3.

Extended European Search Report issued in European Patent Application No. 21777072.6 dated Aug. 3, 2023.

Decision of Rejection issued in corresponding Taiwanese Patent Application No. 110110052, dated Feb. 27, 2025.

International Search Report issued in corresponding International Patent Application No. PCT/JP2021/010798 dated May 25, 2021.

Office Action issued in Chinese Patent Application No. 202180016178.3 dated Jul. 18, 2023.

* cited by examiner

*Primary Examiner* — Kregg T Brooks

(74) *Attorney, Agent, or Firm* — Morgan, Lewis & Bockius LLP

(57) ABSTRACT

A compound including two or more constituent units derived from a monomer M having a radical polymerizable group and having a radical polymerizable group A at the terminal, in which the monomer M includes a monomer m having a structure that generates an active species by photoexcitation.

13 Claims, No Drawings

COMPOUND AND POLYMER COMPOSITION INCLUDING SAID COMPOUND

This application is a continuation application of International Application No. PCT/JP2021/010798, filed on Mar. 17, 2021, which claims the benefit of priority of the prior Japanese Patent Application No. 2020-53216, filed Mar. 24, 2020, the content of which is incorporated herein by reference.

TECHNICAL FIELD

The present invention relates to a compound effective for improving the performance of an adhesive such as adhesive strength and holding power or the like, and a polymer composition including the compound.

BACKGROUND ART

Compounds that form cross-linked structures with polymers are used to improve physical properties in various applications such as paints, films, molding materials, adhesives, and bonding agents.

For example, Patent Document 1 describes an adhesive sheet including a (meth)acrylic copolymer having a radiation-reactive moiety and a plasticizer capable of forming a bond with the (meth)acrylic copolymer by irradiation with radiation.

CITATION LIST

Patent Document

Patent Document 1

Japanese Unexamined Patent Application, First Publication No. 2013-40256

SUMMARY OF INVENTION

Technical Problem

However, the adhesive obtained by the method described in Patent Document 1 had insufficient adhesive strength and holding power. The purpose of the present invention is to solve these problems.

Solution to Problem

The first aspect of the present invention is a compound including two or more constituent units derived from a monomer M having a radical polymerizable group, and a radical polymerizable group A at a terminal, in which the monomer M includes a monomer m having a structure that generates an active species by photoexcitation. A second aspect of the present invention is a polymer composition including the compound described above and a polymer. A third aspect of the present invention is a (meth)acrylic copolymer including a constituent unit derived from a monomer m having a structure that generates an active species by photoexcitation. A fourth aspect of the present invention is a polymer composition including the (meth) acrylic copolymer described above, and a compound. A fifth aspect of the present invention is an adhesive formed by irradiating the polymer composition described above with ultraviolet light. A sixth aspect of the present invention is an adhesive sheet including an adhesive layer, in which the adhesive layer includes the polymer composition. A seventh aspect of the present invention is an adhesive sheet including an adhesive layer, in which the adhesive layer includes the adhesive formed by irradiation with ultraviolet light.

The present invention has the following aspects.

[1]

A compound including two or more constituent units derived from a monomer M having a radical polymerizable group, and a radical polymerizable group A at a terminal, in which the monomer M includes a monomer m having a structure that generates an active species by photoexcitation.

[2]

The compound according to [1], in which the active species generated by photoexcitation is a radical.

[3]

The compound according to [1] or [2], in which the monomer m has a structure represented by Formula 1,

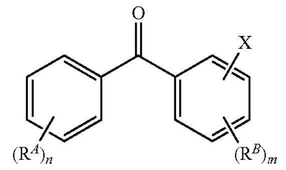

1

(in the formula, $R^A$ and $R^B$ each independently indicate an alkyl group, an alkoxy group, a hydroxyl group, a carboxy group, or a halogen atom, n indicates an integer of 0 to 5, m indicates an integer of 0 to 4, and X indicates a (meth)acryloyloxy group or a (meth) acryloyloxyalkyleneoxy group).

[4]

The compound according to [1] to [3], in which a content of a constituent unit derived from the monomer m in the compound is preferably 0.01% by mass or more and 50% by mass or less with respect to a total mass of the compound and more preferably 5% by mass or more and 40% by mass or less.

[5]

The compound according to [1] to [4], in which the monomer M includes (meth)acrylate having an alicyclic structure.

[6]

The compound according to [1] to [5], in which a weight average molecular weight measured by gel permeation chromatography is preferably 1,000 or more and 100,000 or less and more preferably 2,000 or more and 50,000 or less.

[7]

The compound according to [1] to [6], which has a structure represented by Formula 2,

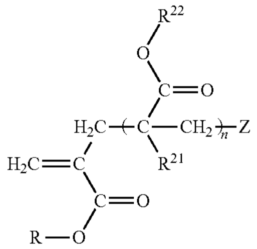

2

(in the formula, R is a group having a structure that generates an active species by photoexcitation, or a linear or branched alkyl group with 1 to 30 carbon atoms, an unsubstituted or substituted group-having alicyclic group, an unsubstituted or substituted group-having aryl group, or an unsubstituted or substituted group-having heterocyclic group, Z is a terminal group, a plurality of $R^{21}$ each independently indicate a hydrogen atom or a methyl group, a plurality of $R^{22}$ each independently indicate a group having a structure that generates an active species by photoexcitation, an unsubstituted or substituted group-having alkyl group, an unsubstituted or substituted group-having alicyclic group, an unsubstituted or substituted group-having aryl group, an unsubstituted or substituted group-having heteroaryl group, an unsubstituted or substituted group-having aralkyl group, an unsubstituted or substituted group-having alkaryl group, an unsubstituted or substituted group-having organosilyl group, or an unsubstituted or substituted group-having (poly)organosiloxane group, the substituted groups in these groups are respectively at least one selected from the group consisting of an alkyl group, an aryl group, a heteroaryl group, a non-aromatic heterocyclic group, an aralkyl group, an alkaryl group, a carboxy group, an alkyloxycarbonylalkyl group, an alkylcarbonyloxyalkyl group, an epoxy group, a hydroxy group, an alkoxy group, a primary amino group, a secondary amino group, a tertiary amino group, an isocyanato group, a sulfonic acid group, and a halogen atom, and n indicates a natural number of 2 or more).

[8]

Examples of the alicyclic structure described above include cyclopropyl groups, cyclobutyl groups, cyclopentyl groups, cyclohexyl groups, cycloheptyl groups, cyclooctyl groups, and the like. In addition, the compound according to [5], in which the polycyclic alicyclic group is a norbornyl group, an isobornyl group, a tricyclononyl group, a tricyclododecyl group, or a tetracyclododecyl group.

[9]

The compound according to [1] to [8], in which, in Formula 2, at least one of R or the plurality of $R^{22}$ is a group having a structure that generates an active species by photoexcitation.

[10]

The compound according to [1] to [9], in which the monomer m is 4-acryloyloxybenzophenone, 4-methacryloyloxybenzophenone, 4-[2-(acryloyloxy)ethoxy]benzophenone, 4-[2-(methacryloyloxy)ethoxy]benzophenone, 2-hydroxy-4-acryloyloxybenzophenone, 2-hydroxy-4-methacryloyloxybenzophenone, 2-hydroxy-4-(2-(acryloyloxy)ethoxybenzophenone, 2-hydroxy-4-(2-methyl-2-acryloyloxy)ethoxybenzophenone, 2-hydroxy-4-acryloyloxy-5-tert-butylbenzophenone, or 2-hydroxy-4-acryloyloxy-2',4'-dichlorobenzophenone.

[11]

A polymer composition including the compound according to any one of [1] to [10], and a polymer other than the compound.

[12]

The polymer composition according to [11], in which the polymer is a polymer with a glass transition temperature of 0° C. or lower.

[13]

The polymer composition according to [11] or [12], in which the polymer is a (meth)acrylic copolymer.

[14]

The polymer composition according to [13], in which the (meth)acrylic copolymer includes a constituent unit derived from a monomer represented by Formula 1,

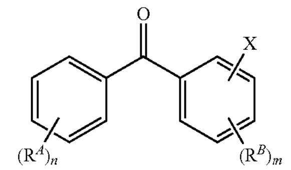

1

(in the formula, $R^A$ and $R^B$ each independently indicate an alkyl group, an alkoxy group, a hydroxyl group, a carboxy group, or a halogen atom, n indicates an integer of 0 to 5, m indicates an integer of 0 to 4, and X indicates a (meth)acryloyloxy group or a (meth)acryloyloxyalkyleneoxy group).

[15]

The polymer composition according to [13] or [14], in which the (meth)acrylic copolymer includes a constituent unit derived from a carboxy group-containing (meth)acrylic monomer.

[16]

The polymer composition according to [15], in which the carboxy group-containing (meth)acrylic monomer is (meth)acrylic acid, 2-(meth)acryloyloxyethyl hexahydro phthalic acid, 2-(meth)acryloyloxypropyl hexahydro phthalic acid, 2-(meth)acryloyloxyethyl phthalic acid, 2-(meth)acryloyloxypropyl phthalic acid, 2-(meth)acryloyloxyethyl maleic acid, 2-(meth)acryloyloxypropyl maleic acid, 2-(meth)acryloyloxyethyl succinic acid, or 2-(meth)acryloyloxypropyl succinic acid.

[17]

The polymer composition according to [15] or [16], in which the content of the constituent unit derived from a carboxy group-containing (meth)acrylic monomer is preferably 0.1 to 20% by mass with respect to a total mass of the (meth)acrylic copolymer, more preferably 0.5 to 10% by mass, and even more preferably 1 to 6% by mass.

[18]

The polymer composition according to [13] to [17], in which a weight average molecular weight (Mw) of the (meth)acrylic copolymer, as measured by gel permeation chromatography (GPC), is preferably 5,000 to 2,000,000, more preferably 10,000 to 1,000,000, and even more preferably 30,000 to 350,000.

[19]

The polymer composition according to [13] to [18], in which a glass transition temperature (Tg) of the (meth) acrylic copolymer is preferably −100° C. or higher and 0° C. or lower and more preferably −80° C. or higher and −5° C. or lower.

[20]

The polymer composition according to [11] to [19], in which a ratio (mass ratio) of the compound to the polymer is preferably in a range of 1:3 to 0.5:99.5, and more preferably 1:9 to 1:70.

[21]

The polymer composition according to [11] to [20], in which, when an adhesive layer is formed, a melt viscosity when measured at 130° C. and a frequency of 0.02 Hz is preferably 10 to 300 Pa-s and more preferably 20 to 200 Pa-s.

[22]

The polymer composition according to [11] to [21], in which, when an adhesive layer is formed, a peel strength (N/25 mm) is preferably 5 to 20 N/25 mm and more preferably 10 to 17 N/25 mm.

[23]

The polymer composition according to [11] to [22], in which, when an adhesive layer is formed, attached to a SUS plate, and a load of 1.0 kg is applied with the other end of the adhesive layer down at 40° C., a holding time is preferably 50,000 seconds or more and more preferably 86,400 seconds or more.

[24]

The polymer composition according to [11] to [23], in which, when an adhesive layer is formed, attached to a SUS plate, and a load of 1.0 kg is applied with the other end of the adhesive layer down at 80° C., the holding time is preferably 1,500 seconds or more, more preferably 3,000 seconds or more, and even more preferably 20,000 seconds or more.

[25]

The polymer composition according to [11] to [24], in which, when an adhesive layer is formed, attached to a SUS plate, and the adhesive layer is peeled off, a glue residue area with respect to the surface area of the SUS plate is preferably 0 area % or more and less than 20 area % and more preferably 0 area %.

[26]

A use of the polymer composition according to [11] to [25] as an adhesive composition in manufacturing.

[27]

An adhesive composition including the polymer composition according to [11] to [25].

[28]

An adhesive formed by irradiating the adhesive composition according to [27] with ultraviolet light.

[29]

The adhesive according to [28], in which an irradiation energy of the ultraviolet light is preferably 10 mJ/cm$^2$ or more and 500 mJ/cm$^2$ or less and more preferably 20 mJ/cm$^2$ or more and 300 mJ/cm$^2$ or less.

[30]

An adhesive sheet including an adhesive layer, in which the adhesive layer includes the adhesive composition according to [27].

[31]

An adhesive sheet including an adhesive layer, in which the adhesive sheet includes the adhesive formed by irradiation with ultraviolet light according to [28] or [29].

[32]

A (meth)acrylic copolymer including a constituent unit derived from a monomer m having a structure that generates an active species by photoexcitation.

[33]

The (meth)acrylic copolymer according to [32], in which the monomer m is a monomer represented by Formula 1,

1

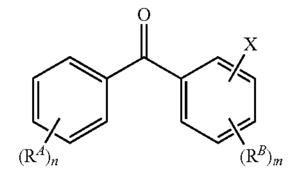

(in the formula, $R^A$ and $R^B$ each independently indicate an alkyl group, an alkoxy group, a hydroxyl group, a carboxy group, or a halogen atom, n indicates an integer of 0 to 5, m indicates an integer of 0 to 4, and X indicates a (meth)acryloyloxy group or a (meth) acryloyloxyalkyleneoxy group).

[34]

The (meth)acrylic copolymer according to [32] or [33], in which the (meth)acrylic copolymer includes a constituent unit derived from a carboxy group-containing (meth)acrylic monomer.

[35]

The (meth)acrylic copolymer according to [34], in which the carboxy group-containing (meth)acrylic monomer is a (meth)acrylic acid, 2-(meth)acryloyloxyethyl hexahydro phthalic acid, 2-(meth)acryloyloxypropyl hexahydro phthalic acid, 2-(meth)acryloyloxyethyl phthalic acid, 2-(meth)acryloyloxypropyl phthalic acid, 2-(meth)acryloyloxyethyl maleic acid, 2-(meth)acryloyloxypropyl maleic acid, 2-(meth)acryloyloxyethyl succinic acid, or 2-(meth) acryloyloxypropyl succinic acid.

[36]

The (meth)acrylic copolymer according to [34] or [35], in which a content of the constituent units derived from a carboxy group-containing (meth)acrylic monomer is preferably 0.1 to 20% by mass with respect to the total mass of the (meth)acrylic copolymer, more preferably 0.5 to 10% by mass, and more preferably 1 to 6% by mass.

[37]

The (meth)acrylic copolymer according to [32] to [36], in which a weight average molecular weight (Mw) of the (meth)acrylic copolymer, as measured by gel permeation chromatography (GPC), is preferably 5,000 to 2,000,000, more preferably 10,000 to 1,000,000, and even more preferably 30,000 to 350,000.

[38]

The (meth)acrylic copolymer according to [32] to [37], in which a glass transition temperature (Tg) of the (meth) acrylic copolymer is preferably −100° C. or higher and 0° C. or lower and more preferably −80° C. or higher and −5° C. or lower.

[39]

A polymer composition including the (meth)acrylic copolymer according to any one of [32] to [38], and a compound having a radical polymerizable group A at the terminal and including two or more constituent units derived from a monomer M having a radical polymerizable group.

[40]

The polymer composition according to [39], in which a ratio (mass ratio) of the compound to the polymer is preferably in a range of 1:3 to 0.5:99.5, and more preferably 1:9 to 1:70.

[41]

The polymer composition according to [39] or [40], in which, when an adhesive layer is formed, a melt viscosity when measured at 130° C. and a frequency of 0.02 Hz is preferably 10 to 300 Pa-s and more preferably 20 to 200 Pa-s.

[42]

The polymer composition according to [39] to [41], in which, when the adhesive layer is formed, a peel strength (N/25 mm) is preferably 5 to 20 N/25 mm and more preferably 10 to 17 N/25 mm.

[43]

The polymer composition according to [39] to [42], in which, when the adhesive layer is formed, attached to a SUS plate, and a load of 1.0 kg is applied with the other end of the adhesive layer down at 40° C., a holding time is preferably 50,000 seconds or more and more preferably 86,400 seconds or more.

[44]

The polymer composition according to [39] to [43], in which, when the adhesive layer is formed, attached to a SUS plate, and a load of 1.0 kg is applied with the other end of the adhesive layer down at 80° C., the holding time is preferably 1,500 seconds or more, more preferably 3,000 seconds or more, and even more preferably 20,000 seconds or more.

[45]

The polymer composition according to [39] to [44], in which, when the adhesive layer is formed, attached to a SUS plate, and the adhesive layer is peeled off, a glue residue area with respect to the surface area of the SUS plate is preferably 0 area % or more and less than 20 area % and more preferably 0 area %.

[46]

A use of the polymer composition according to [39] to [45] as an adhesive composition in manufacturing.

[47]

An adhesive composition including the polymer composition according to [39] to [45].

[48]

An adhesive formed by irradiating the adhesive composition according to [47] with ultraviolet light.

[49]

The adhesive according to [48] in which an irradiation energy of the ultraviolet light is preferably 10 $mJ/cm^2$ or more and 500 $mJ/cm^2$ or less and more preferably 20 $mJ/cm^2$ or more and 300 $mJ/cm^2$ or less.

[50]

An adhesive sheet including an adhesive layer, in which the adhesive layer includes the adhesive composition according to [47].

[51]

An adhesive sheet including an adhesive layer, in which the adhesive sheet includes the adhesive formed by irradiation with ultraviolet light according to [48] or [49].

Advantageous Effects of Invention

The compound or (meth)acrylic copolymer of the present invention improve adhesive strength, holding power, and substrate contamination resistance in a case of being used as components of a polymer composition.

DESCRIPTION OF EMBODIMENTS

<<Compound>>

The compound of the present invention is a compound including two or more constituent units derived from a monomer M having a radical polymerizable group, and having a radical polymerizable group A at a terminal, in which the monomer M includes a monomer m having a structure that generates an active species by photoexcitation. It is possible for the compound of the present invention to form a cross-linked structure with other polymers by having a radical polymerizable group A at the terminal. In addition, it is also possible for the compounds of the present invention to polymerize with other monomers and obtain graft copolymers by having a radical polymerizable group A at the terminal.

As the radical polymerizable group A, a group having an ethylenically unsaturated bond is preferable. Examples of groups having an ethylenically unsaturated bond include $CH_2{=}C(COOR){-}CH_2{-}$, a (meth)acryloyl group, a 2-(hydroxymethyl)acryloyl group, a vinyl group, and the like.

Here, R indicates a hydrogen atom, an unsubstituted or substituted group-having alkyl group, an unsubstituted or substituted group-having alicyclic group, an unsubstituted or substituted group-having aryl group, or unsubstituted or substituted group-having heterocyclic group.

As an unsubstituted or substituted group-having alkyl group, an unsubstituted or substituted group-having alkyl group with 1 to 30 carbon atoms is preferable, an unsubstituted or substituted group-having n alkyl group with 1 to 20 carbon atoms is more preferable, and an unsubstituted or substituted group-having alkyl group with 1 to 10 carbon atoms is even more preferable. As an unsubstituted or substituted group-having alicyclic group, an unsubstituted or substituted group-having alicyclic group with 3 to 30 carbon atoms is preferable, an unsubstituted or substituted group-having alicyclic group with 3 to 20 carbon atoms is more preferable, and an unsubstituted or substituted group-having alicyclic group with 3 to 10 carbon atoms is even more preferable. As an unsubstituted or substituted group-having aryl group, an unsubstituted or substituted group-having aryl group with 6 to 30 carbon atoms is preferable, an unsubstituted or substituted group-having aryl group with 6 to 20 carbon atoms is more preferable, and an unsubstituted or substituted group-having aryl group with 6 to 10 carbon atoms is even more preferable. As unsubstituted or substituted group-having heterocyclic groups, unsubstituted or substituted group-having heterocyclic groups with 3 to 30 carbon atoms are preferable, unsubstituted or substituted group-having heterocyclic groups with 3 to 20 carbon atoms are more preferable, and unsubstituted or substituted group-having heterocyclic groups with 3 to 10 carbon atoms are even more preferable.

In addition, it is necessary for the compounds of the present invention to include a constituent unit derived from the monomer m having a structure that generates an active species by photoexcitation. By the compound of the present invention having a structure that generates an active species by photoexcitation, for example, it is possible to mix the compound of the present invention with other polymers and to form a cross-linked structure by irradiation with ultraviolet light.

A structure that generates an active species by photoexcitation is a structure that generates any of radicals, cations, or anions by irradiation with ultraviolet light, electron beams, or the like, and a structure that generates radicals is preferable in terms of reactivity.

Examples of monomers having a structure that generates radicals by photoexcitation include monomers having a benzophenone skeleton, thioxanthone skeleton, anthraquinone skeleton, or the like and benzophenone derivatives represented by Formula 1 are preferable in terms of reactivity.

Examples of the monomer represented by Formula 1 include 4-acryloyloxybenzophenone, 4-methacryloyloxybenzophenone, 4-[2-(acryloyloxy)ethoxy]benzophenone, 4-[2-(methacryloyloxy)ethoxy]benzophenone, 2-hydroxy-4-acryloyloxybenzophenone, 2-hydroxy-4-methacryloyloxybenzophenone, 2-hydroxy-4-(2-(acryloyloxy)ethoxybenzophenone, 2-hydroxy-4-(2-methyl-2-acryloyloxy)ethoxybenzophenone, 2-hydroxy-4-acryloyloxy-5-tert-butylbenzophenone, and 2-hydroxy-4-acryloyloxy-2',4'-dichlorobenzophenone, and 4-methacryloyloxybenzophenone and 4-[2-(methacryloyloxy)ethoxy]benzophenone are particularly preferable.

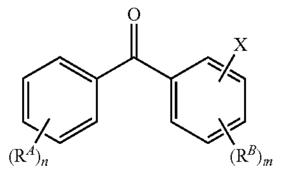

(In the formula, $R^A$ and $R^B$ each independently indicate an alkyl group, an alkoxy group, a hydroxyl group, a carboxy group, or a halogen atom, n indicates an integer of 0 to 5, m indicates an integer of 0 to 4, and X indicates a (meth) acryloyloxy group or a (meth)acryloyloxyalkyleneoxy group).

The content of the constituent unit derived from the monomer m in the compound of the present invention is preferably 0.01% by mass or more and 50% by mass or less with respect to the total mass of the compound. The content of the constituent units derived from the monomer m in the compound is preferably higher in terms of improving the holding power in a case of being used as a polymer composition and a lower content is preferable in terms of compatibility with other components. In terms of balancing performance, the content of the constituent unit derived from the monomer m in the compound is more preferably 1% by mass or more and 40% by mass or less. In the present specification, it is possible to calculate the content of the constituent unit from the charge-in amount of monomer forming the constituent unit.

In Formula 1, $R^A$ and $R^B$ each independently indicate an alkyl group, an alkoxy group, a hydroxyl group, a carboxy group, or a halogen atom. As alkyl groups, linear or branched alkyl groups with 1 to 10 carbon atoms are preferable and linear or branched alkyl groups with 1 to 5 carbon atoms are more preferable. As alkoxy groups, linear or branched alkoxy groups with 1 to 10 carbon atoms are preferable and linear or branched alkoxy groups with 1 to 5 carbon atoms are more preferable. Examples of halogen atoms include fluorine atoms, chlorine atoms, bromine atoms, and iodine atoms. n is an integer of 0 to 5, preferably 0 to 3, and more preferably 0. m is an integer of 0 to 4, preferably 0 to 3, and more preferably 0. X indicates a (meth)acryloyloxy group or a (meth)acryloyloxyalkyleneoxy group. As an alkylene group in the (meth)acryloyloxyalkyleneoxy group, an alkylene group with 2 to 10 carbon atoms is preferable and an alkylene group with 2 to 6 carbon atoms is more preferable. Examples of the (meth)acryloyloxyalkyleneoxy groups include 2-(meth)acryloyloxyethoxy groups, 2-(meth)acryloyloxypropoxy groups, and the like.

In addition, examples of monomers other than the monomer m included in the monomer M include hydrocarbon group-containing (meth)acrylic acid esters, hydroxyl group-containing (meth)acrylic acid esters, carboxyl group-containing vinyl-based monomers, acid anhydride group-containing vinyl-based monomers, unsaturated dicarboxylic acid diester monomers, epoxy group-containing vinyl-based monomers, vinyl-based monomers such as vinyl propionate, multifunctional vinyl-based monomers, and the like.

In hydrocarbon group-containing (meth)acrylic acid esters, as the hydrocarbon groups, unsubstituted or substituted group-having hydrocarbon groups with 1 to 30 carbon atoms are preferable, unsubstituted or substituted group-having hydrocarbon groups with 1 to 20 carbon atoms are more preferable, and unsubstituted or substituted group-having hydrocarbon groups with 1 to 10 carbon atoms are even more preferable. For example, as hydrocarbon groups, linear or branched alkyl groups, linear or branched alkenyl groups, linear or branched alkynyl groups, linear or branched cycloalkyl groups, and linear or branched aryl groups are preferable. Examples thereof include hydrocarbon group-containing (meth)acrylic acid esters such as methyl (meth)acrylate, ethyl (meth)acrylate, n-propyl (meth)acrylate, isopropyl (meth)acrylate, n-butyl (meth) acrylate, isobutyl (meth)acrylate, t-butyl (meth)acrylate, isoamyl (meth)acrylate, hexyl (meth)acrylate, 2-ethylhexyl (meth)acrylate, octyl (meth)acrylate, lauryl (meth)acrylate, stearyl (meth)acrylate, isostearyl (meth)acrylate, hexadecyl (meth)acrylate, nonyl (meth)acrylate, isononyl (meth)acrylate, phenyl (meth)acrylate, benzyl (meth)acrylate, cyclohexyl (meth)acrylate, tetrahydrofurfuryl (meth)acrylate, isobornyl (meth)acrylate, 3,5,5-trimethylcyclohexyl (meth) acrylate, dicyclopentanyl (meth)acrylate, dicyclopentenyl (meth)acrylate, dicyclopentenyloxyethyl (meth)acrylate, terpene acrylate or derivatives thereof, hydrogenated rosin acrylate or derivatives thereof, and docosyl (meth)acrylate; hydroxyl group-containing (meth)acrylic acid esters such as 2-hydroxyethyl (meth)acrylate, 2-hydroxypropyl (meth) acrylate, 2-hydroxybutyl (meth)acrylate, 3-hydroxybutyl (meth)acrylate, 4-hydroxybutyl (meth)acrylate, and glycerol (meth)acrylate; carboxyl group-containing vinyl-based monomers such as (meth)acrylic acid, 2-(meth)acryloyloxyethyl hexahydro phthalic acid, 2-(meth)acryloyloxypropyl hexahydro phthalic acid, 2-(meth)acryloyloxyethyl phthalic acid, 2-(meth)acryloyloxypropyl phthalic acid, 2-(meth) acryloyloxyethyl maleic acid, 2-(meth)acryloyloxypropyl maleic acid, 2-(meth)acryloyloxyethyl succinic acid, 2-(meth)acryloyloxypropyl succinic acid, crotonic acid, fumaric acid, maleic acid, itaconic acid, citraconic acid, monomethyl maleate, monoethyl maleate, monooctyl maleate, monomethyl itaconic acid, monoethyl itaconic acid, monobutyl itaconic acid, monooctyl itaconic acid, monomethyl fumaric acid, monoethyl fumaric acid, monobutyl fumaric acid, monooctyl fumaric acid, and monoethyl citraconic acid; acid anhydride group-containing vinyl-based monomers such as maleic anhydride and itaconic anhydride; unsaturated dicarboxylic acid diester monomers such as dimethylmalate, dibutylmalate, dimethylfumalate, dibutylfumalate, dibutylitaconate, and diperfluorocyclohexylfumalate; epoxy group-containing vinyl-based monomers such as glycidyl (meth)acrylate, glycidyl α-ethyl acrylate, and 3,4-epoxybutyl (meth)acrylate; amino group-containing (meth)acrylic acid ester-based vinyl-based monomers such as dimethylaminoethyl (meth)acrylate and diethylaminoethyl (meth)acrylate; amide group-containing vinyl-based monomers such as (meth)acrylamide, N-t-butyl (meth)acrylamide, N-methylol (meth)acrylamide, N-isopropylacrylamide, hydroxyethylacrylamide, N-methoxymethyl (meth)acrylamide, N-butoxymethyl (meth)acrylamide, diacetone acrylamide, maleic acid amide, and maleimide; vinyl-based monomers such as styrene, α-methylstyrene, vinyl toluene, (meth)acrylonitrile, vinyl acetate, and vinyl propionate; multifunctional vinyl-based monomers such as divinylbenzene, ethylene glycol di(meth)acrylate, 1,3-butylene glycol di(meth)acrylate, 1,4-butanediol di(meth)acrylate, 1,6-hexanediol di(meth)acrylate, diethylene glycol di(meth) acrylate, triethylene glycol di(meth)acrylate, tetraethylene glycol di(meth)acrylate, polyethylene glycol di(meth)acrylate, tripropylene glycol di(meth)acrylate, neopentyl glycol di(meth)acrylate, 1,9-nonanediol di(meth)acrylate, 1,10-decanediol di(meth)acrylate, trimethylolpropane tri(meth) acrylate, pentaerythritol tetra(meth)acrylate, dipentaerythritol hexa(meth)acrylate, allyl (meth)acrylate, triallyl cyanurate, diallyl maleate, polypropylene glycol diallyl ether, and N,N'-methylenebis (meth)acrylamide; acryloyl morpholine, polyethylene glycol (meth)acrylate, polypropylene glycol (meth)acrylate, methoxyethyl (meth)acrylate, ethoxyethyl (meth)acrylate, n-butoxyethyl (meth)acrylate, isobutoxyethyl (meth)acrylate, t-butoxyethyl (meth)acrylate, ethoxyethoxyethyl (meth)acrylate, phenoxyethyl (meth)acrylate, nonylphenoxyethyl (meth)acrylate, 3-methoxybutyl (meth)acrylate, acetoxyethyl (meth)acrylate, “Placcel (registered trademark, the same applies below) FM” (caprolactone-added monomer, manufactured by Daicel Corporation, trade name), “Blemmer (registered trademark, the same applies below) PME-100” (methoxy polyethylene glycol methacrylate (with 2 ethylene glycol chains) manufactured by NOF Corporation, trade name), “Blemmer PME-200” (methoxy polyethylene glycol methacrylate (with 4 ethylene glycol chains) manufactured by NOF Corporation, trade name), “Blemmer PME-400” (methoxy polyethylene glycol methacrylate (with 9 ethylene glycol chains) manufactured by NOF Corporation, trade name), “Blemmer 50 POEP-800B” (octoxy polyethylene glycol-polypropylene glycol-methacrylate (with 8 ethylene glycol chains and 6 propylene glycol chains) manufactured by NOF Corporation, trade name), “Blemmer 20 ANEP-600” (nonylphenoxy(ethylene glycol-polypropylene glycol) monoacrylate manufactured by NOF Corporation, trade name), “Blemmer AME-100” (manufactured by NOF Corporation, trade name), “Blemmer AME-200” (manufactured by NOF Corporation, trade name), “Blemmer 50 AOEP-800B” (manufactured by NOF Corporation, trade name); organosilyl group-containing monomers other than silane coupling agent-containing monomers, such as trimethylsilyl (meth) acrylate, triethylsilyl (meth)acrylate, tri-n-propylsilyl (meth) acrylate, tri-n-butylsilyl(meth)acrylate, tri-n-amylsilyl (meth)acrylate, tri-n-hexylsilyl (meth)acrylate, tri-n-octylsilyl (meth)acrylate, tri-n-dodecylsilyl (meth)acrylate, triphenylsilyl (meth)acrylate, tri-p-methylphenylsilyl (meth) acrylate, tribenzylsilyl (meth)acrylate, triisopropylsilyl (meth)acrylate, triisobutylsilyl (meth)acrylate, tri(s-butyl) silyl (meth)acrylate, tri(2-methylisopropyl) silyl (meth)acrylate, tri(t-butyl) silyl (meth)acrylate, ethyldimethylsilyl (meth)acrylate, n-butyldimethylsilyl (meth)acrylate, diisopropyl (n-butyl) silyl (meth)acrylate, n-octyldi(n-butyl) silyl (meth)acrylate, diisopropylstearylsilyl (meth)acrylate, dicyclohexylphenylsilyl (meth)acrylate, t-butyldiphenylsilyl (meth)acrylate, lauryl diphenylsilyl (meth)acrylate, triisopropylsilyl methylmalate, triisopropylsilyl amylmalate, tri (n-butyl) silyl (n-butyl) malate, (t-butyldiphenylsilyl) (methyl) malate, (t-butyldiphenylsilyl) (n-butyl) malate, (triisopropylsilyl) (methyl) fumarate, (triisopropylsilyl) (amyl) fumarate, (tri(n-butylsilyl)) (n-butyl) fumarate, (t-butyldiphenylsilyl) (methyl) fumarate, (t-butyldiphenylsilyl) (n-butyl) fumarate, Silaplane FM-0711 (manufactured by JNC Corporation, trade name), Silaplane (registered trademark, the same applies below) FM-0721 (manufactured by JNC Corporation, trade name), Silaplane FM-0725 (manufactured by JNC Corporation, trade name), Silaplane TM-0701 (manufactured by JNC Corporation, trade name), Silaplane TM-0701T (manufactured by JNC Corporation, trade name), X-22-174ASX (manufactured by Shin-Etsu Chemical Co., Ltd., trade name), X-22-174BX (manufactured by Shin-Etsu Chemical Co., Ltd., trade name), KF-2012 (manufactured by Shin-Etsu Chemical Co., Ltd., trade name), X-22-2426 (manufactured by Shin-Etsu Chemical Co., Ltd., trade name), and X-22-2404 (manufactured by Shin-Etsu Chemical Co., Ltd., trade name); halogenated olefins such as vinyl chloride, vinylidene chloride, vinyl fluoride, vinylidene fluoride, and chlorotrifluoroethylene; fluorine-containing monomers (excluding halogenated olefins) such as 2,2,2-trifluoroethyl (meth)acrylate, 2,2,3,3,3-pentafluorophenyl (meth)acrylate, 2-(perfluorobutyl) ethyl (meth)acrylate, 3-(perfluorobutyl)-2-hydroxypropyl (meth)acrylate, 2-(perfluorohexyl) ethyl (meth)acrylate, 3-perfluorohexyl-2-hydroxypropyl(meth)acrylate, 3-(perfluoro-3-methylbutyl)-2-hydroxypropyl (meth)acrylate, 2,2,3,3-tetrafluoropropyl (meth)acrylate, 1H,1H,5H-octafluoropentyl (meth)acrylate, 1H,1H,2H,2H-tridecafluorooctyl (meth)acrylate, 1H-1-(trifluoromethyl) trifluoroethyl (meth) acrylate, 1H,1H,3H-hexafluorobutyl (meth)acrylate, and 1,2,2,2-tetrafluoro-1-(trifluoromethyl) ethyl (meth)acrylate; and monomers having an acetal structure such as 1-butoxyethyl (meth)acrylate, 1-(2-ethylhexyloxy) ethyl (meth)acrylate, 1-(cyclohexyloxy) ethyl methacrylate, and 2-tetrahydropyranyl (meth)acrylate.

In addition, in terms of improving the heat resistance and moisture resistance of the polymer composition, the monomer M preferably includes (meth)acrylate having an alicyclic structure. An alicyclic structure refers to an organic group including an alicyclic ring and the alicyclic group may be a monocyclic or polycyclic. Examples of monocyclic alicyclic groups include cyclopropyl groups, cyclobutyl groups, cyclopentyl groups, cyclohexyl groups, cycloheptyl groups, cyclooctyl groups, and the like. In addition, examples of polycyclic alicyclic groups include norbornyl groups, isobornyl groups, tricyclononyl groups, tricyclododecyl groups, tetracyclododecyl groups, and the like. In addition, the hydrogen atoms of these alicyclic groups may be substituted with alkyl groups, alkoxy groups, hydroxyl groups, and the like. As a (meth)acrylate having an alicyclic structure, isobornyl (meth)acrylate is particularly preferable. Two or more of these monomers may be used in combination.

The weight average molecular weight (Mw) of the compound of the present invention, as measured by gel permeation chromatography (GPC), is preferably 1,000 or more and 100,000 or less. The Mw is preferably higher in terms of improving the holding power in a case of being used as a polymer composition and lower in terms of manufacturing stability. The Mw is more preferably 2,000 or more and 50,000 or less in terms of performance balance. In addition, as the compound, a structure represented by Formula 2 is preferable.

2

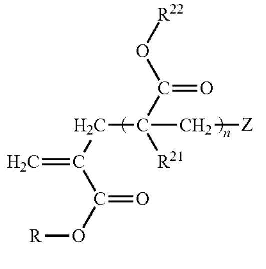

(In the formula, R is a group having a structure that generates an active species by photoexcitation, or a linear or branched alkyl group with 1 to 30 carbon atoms, an unsubstituted or substituted group-having alicyclic group, an unsubstituted or substituted group-having aryl group, or an unsubstituted or substituted group-having heterocyclic group, Z is a terminal group, the plurality of $R^{21}$ each independently indicate a hydrogen atom or a methyl group, the plurality of $R^{22}$ each independently indicate a group having a structure that generates an active species by photoexcitation, an unsubstituted or substituted group-having alkyl group, an unsubstituted or substituted group-having alicyclic group, an unsubstituted or substituted group-having aryl group, an unsubstituted or substituted group-having heteroaryl group, an unsubstituted or substituted group-having aralkyl group, an unsubstituted or substituted group-having alkaryl group, an unsubstituted or substituted group-having organosilyl group, or an unsubstituted or substituted group-having (poly)organosiloxane group, the substituted groups in these groups are respectively at least one selected from the group consisting of an alkyl group, an aryl group, a heteroaryl group, a non-aromatic heterocyclic group, an aralkyl group, an alkaryl group, a carboxy group, an alkyloxycarbonylalkyl group, an alkylcarbonyloxyalkyl group, an epoxy group, a hydroxy group, an alkoxy group, a primary amino group, a secondary amino group, a tertiary amino group, an isocyanato group, a sulfonic acid group, and a halogen atom, and n indicates a natural number of 2 or more. Examples of the terminal group in Z include a hydrogen atom or a group derived from a radical polymerization initiator, in the same manner as the terminal groups of polymers obtained by known radical polymerization).

In the compound represented by Formula 2, for n of $R^{21}$ and $R^{22}$, it is possible to select independent groups, respectively. Here, at least two of R or a plurality of $R^{22}$ are preferably groups having a structure that generates an active species by photoexcitation. For example, it is possible to select a compound in which R is a linear or branched alkyl group with 1 to 30 carbon atoms or an alicyclic group, a plurality of $R^{21}$ are each independently a hydrogen atom or a methyl group, at least two of a plurality of $R^{22}$ are groups having a structure that generates an active species by photoexcitation, and the other $R^{22}$ are each independently linear or branched alkyl groups with 1 to 30 carbon atoms or alicyclic groups. Specifically, when n=3, it is possible to select a compound in which R is a linear or branched alkyl group with 1 to 30 carbon atoms or an alicyclic group, the first to third $R^{21}$ are hydrogen atoms or methyl groups, the first $R^{22}$ is a linear or branched alkyl group with 1 to 30 carbon atoms or an alicyclic group, and the second and third $R^{22}$ are groups having a structure that generates an active species by photoexcitation.

Examples of structures that generate an active species by photoexcitation include a benzophenone skeleton, a thioxanthone skeleton, an anthraquinone skeleton, and the like.

Examples of groups having a structure that generates an active species by photoexcitation include groups in which one hydrogen atom is removed from an unsubstituted or substituted group-having benzophenone, groups in which one hydrogen atom is removed from an unsubstituted or substituted group-having thioxanthone, groups in which one hydrogen atom is removed from an unsubstituted or substituted group-having anthraquinone, and the like.

Examples of these substituted groups include linear or branched alkyl groups with 1 to 30 carbon atoms, linear or branched alkoxy groups with 1 to 30 carbon atoms, hydroxyl groups, halogen atoms, and the like.

Linear or branched alkyl groups with 1 to 30 carbon atoms are preferably linear or branched alkyl groups with 1 to 20 carbon atoms, more preferably linear or branched alkyl groups with 1 to 10 carbon atoms, and even more preferably linear or branched alkyl groups with 1 to 5 carbon atoms.

Examples of groups derived from radical polymerization initiators include alkyl carbonyloxy groups with 1 to 30 carbon atoms, linear or branched alkyl groups with 1 to 30 carbon atoms, aryl carbonyloxy groups with 6 to 30 carbon atoms, aryl groups with 6 to 30 carbon atoms, and the like. Examples thereof include 1,1,3,3-tetramethylbutyl groups, 2-ethylhexylcarbonyloxy groups, and the like.

Unsubstituted or substituted group-having alkyl groups are preferably unsubstituted or substituted group-having linear or branched alkyl groups with 1 to 30 carbon atoms, more preferably unsubstituted or substituted group-having linear or branched alkyl groups with 1 to 20 carbon atoms, even more preferably unsubstituted or substituted group-having linear or branched alkyl group with 1 to 10 carbon atoms, and particularly preferably unsubstituted or substituted group-having linear or branched alkyl group with 1 to 5 carbon atoms. As an unsubstituted or substituted group-having alicyclic group, an unsubstituted or substituted group-having alicyclic group with 3 to 30 carbon atoms is preferable, an unsubstituted or substituted group-having alicyclic group with 3 to 20 carbon atoms is more preferable, and an unsubstituted or substituted group-having alicyclic group with 3 to 10 carbon atoms is even more preferable. As an unsubstituted or substituted group-having aryl group, an unsubstituted or substituted group-having aryl group with 6 to 30 carbon atoms is preferable, an unsubstituted or substituted group-having aryl group with 6 to 20 carbon atoms is more preferable, and an unsubstituted or substituted group-having aryl group with 6 to 10 carbon atoms is even more preferable. As an unsubstituted or substituted group-having heteroaryl group, an unsubstituted or substituted group-having heteroaryl group with 2 to 30 carbon atoms is preferable, an unsubstituted or substituted group-having heteroaryl group with 2 to 20 carbon atoms is more preferable, and an unsubstituted or substituted group-having heteroaryl group with 2 to 10 carbon atoms is even more preferable. As an unsubstituted or substituted group-having aralkyl group, an unsubstituted or substituted group-having aralkyl group with 6 to 30 carbon atoms is preferable, an unsubstituted or substituted group-having aralkyl group with 6 to 20 carbon atoms is more preferable, and an unsubstituted or substituted group-having aralkyl group with 6 to 10 carbon atoms is even more preferable. As an unsubstituted or substituted group-having alkaryl group (alkylaryl group), an unsubstituted or substituted group-having alkaryl group with 6 to 30 carbon atoms is preferable, an unsubstituted or substituted group-having alkaryl group with 6 to 20 carbon atoms is more preferable, and an unsubstituted or substituted group-having alkaryl group with 6 to 10 carbon atoms is even more preferable. As an unsubstituted or substituted group-having organosilyl group, an unsubstituted or substituted group-having organosilyl group with 1 to 30 carbon atoms is preferable, an unsubstituted or substituted group-having organosilyl group with 1 to 20 carbon atoms is more preferable, an unsubstituted or substituted group-having organosilyl group with 1 to 10 carbon atoms is even more preferable. As an unsubstituted or substituted group-having (poly)organosiloxane group, an unsubstituted or substituted group-having (poly)organosiloxane group with 1 to 30 carbon atoms is preferable, an unsubstituted or substituted group-having (poly)organosiloxane group with 1 to 20 carbon atoms is more preferable, and an unsubstituted or substituted group-having (poly)organosiloxane groups with 1 to 10 carbon atoms is even more preferable. Alkyl groups with 1 to 5 carbon atoms are preferable as alkyl group substituted groups. Aryl groups with 6 to 10 carbon atoms are preferable as aryl group substituted groups. Heteroaryl groups with 4 to 10 carbon atoms are preferable as heteroaryl group substituted groups. Non-aromatic heterocyclic groups with 5 to 10 carbon atoms are preferable as non-aromatic heterocyclic group substituted groups. Aralkyl groups with 6 to 10 carbon atoms are preferable as aralkyl group substituted groups. Alkaryl groups with 6 to 10 carbon atoms are preferable as alkaryl group (alkylaryl groups) substituted groups. Alkyloxycarbonylalkyl groups with 3 to 10 carbon atoms are preferable as alkyloxycarbonylalkyl group substituted groups. Alkylcarbonyloxyalkyl groups with 3 to 10 carbon atoms are preferable as alkylcarbonyloxyalkyl group substituted groups. Alkoxy groups with 1 to 5 carbon atoms are preferable as alkoxy group substituted groups. Secondary amino groups having one alkyl group with 1 to 5 carbon atoms are preferable as secondary amino group substituted groups. Tertiary amino groups having two alkyl groups with 1 to 5 carbon atoms are preferable as tertiary amino group substituted groups. As halogen atom substituted groups, fluorine atoms, bromine atoms, chlorine atoms, and iodine atoms are preferable.

The compounds of the present invention may be formed by polymerizing a mixture of monomers including the monomer M having a radical polymerizable group by a known method and examples thereof include a method using a cobalt chain transfer agent (U.S. Pat. No. 4,680,352), a method using an α-substituted unsaturated compound such as α-bromomethylstyrene as a chain transfer agent (International Publication No. 88/04304), a method of chemically bonding polymerizable groups (Patent Publication No. 60-133007), a method using thermal decomposition (Patent Publication No. 11-240854), and the like. Among the above, a method using a cobalt chain transfer agent is preferable in terms of having fewer manufacturing steps and of using a catalyst with a high chain transfer constant.

For a compound including two or more constituent units derived from a monomer M having a radical polymerizable group, and a radical polymerizable group A at a terminal, in which the monomer M includes a monomer m having a structure that generates an active species by photoexcitation, it is possible to confirm the presence or absence of the content by analysis methods such as nuclear magnetic resonance (NMR). For example, when the terminal radical polymerizable group A has an unsaturated hydrocarbon structure such as $CH_2{=}C{-}$, it is possible to confirm a peak derived from the unsaturated hydrocarbon structure in a range where the chemical shift is 4 ppm to 7 ppm when measured in a proton nuclear magnetic resonance apparatus, with a solvent of heavy chloroform, a measurement nucleus of $^1H$, a measuring temperature of 35° C., and a number of integrations of 1024 times. In addition, for the structure derived from the monomer m having a structure that generates an active species by photoexcitation, for example, in the case of having an aromatic ring hydrocarbon structure, it is possible to confirm a peak derived from the aromatic ring hydrocarbon structure in a range where the chemical shift is 6 ppm to 9 ppm when measured in a proton nuclear magnetic resonance apparatus, with a solvent of heavy chloroform, a measurement nucleus of $^1H$, a measuring temperature of 35° C., and a number of integrations of 1024 times.

Since the compound of the present invention includes two or more constituent units derived from a monomer M having a radical polymerizable group, and a radical polymerizable group A at a terminal, use is possible as a monomer for synthesizing a polymer, also known as a macromonomer.

<<Polymer Composition>>

It is possible to use the compound of the present invention as a polymer composition by mixing with other polymers (simply referred to below as "polymers") other than the compounds described above. For the polymer composition, the radical polymerizable group A at the terminal of the compound of the present invention and the structure that generates an active species by photoexcitation form a cross-linked structure with the polymer to improve the aggregation strength of the polymer composition.

<Polymer>

The polymer included in the polymer composition of the present invention has substantially no radical polymerizable group A at the terminal.

The polymer may be a polymer of a single monomer (homopolymer) or a copolymer of a plurality of monomers (copolymer). In addition, the polymer may be any of a random copolymer, a block copolymer, or a graft copolymer.

In addition, the polymer is preferably an adhesive polymer. By forming a cross-linked structure in the polymer composition by irradiation with ultraviolet light or the like, the adhesive strength, holding power, and substrate contamination resistance of the polymer composition are improved.

The glass transition temperature of the polymer is preferably 0° C. or lower in terms of melt viscosity and more preferably −10° C. or lower. Specifically, the glass transition temperature of the polymer is preferably −100 to 0° C. and more preferably −80 to −5° C. The glass transition temperature (Tg) is the value obtained by converting the absolute temperature (K) calculated from the equation below into degrees Celsius (° C.).

$$1/Tg=\Sigma(w_i/Tg_i)$$

In the equation described above, $w_i$ indicates the mass fraction of a monomer i forming the polymer and $Tg_i$ indicates the glass transition temperature of the homopolymer of the monomer i forming the polymer.

Tg and $Tg_i$ in the formula described above are values expressed in absolute temperature (K). In addition, the glass transition temperature of the homopolymer of monomer i is a value described in the Polymer Handbook [Polymer HandBook, J. J. Brandrup, Interscience, 1989].

Furthermore, the polymer is preferably a (meth)acrylic copolymer in terms of adhesive properties. The (meth)acrylic copolymer means a copolymer in which at least some of the constituent units are constituent units derived from (meth)acrylic monomers. The (meth)acrylic copolymer may further include constituent units derived from monomers other than (meth)acrylic monomers (for example, styrene and the like). The (meth)acrylic monomer means a monomer having (meth)acryloyl groups and examples thereof include the same (meth)acrylic monomers as the monomers forming the compound of the present invention.

In addition, since the adhesive strength is improved, the (meth)acrylic copolymer preferably includes a constituent unit derived from a carboxy group-containing (meth)acrylic monomer. Examples of the carboxy group-containing (meth)acrylic monomer include (meth)acrylic acid, 2-(meth)acryloyloxyethyl hexahydro phthalic acid, 2-(meth)acryloyloxypropyl hexahydro phthalic acid, 2-(meth)acryloyloxyethyl phthalic acid, 2-(meth)acryloyloxypropyl phthalic acid, 2-(meth)acryloyloxyethyl maleic acid, 2-(meth)acryloyloxypropyl maleic acid, 2-(meth)acryloyloxyethyl succinic acid, 2-(meth)acryloyloxypropyl succinic acid, and the like.

The content of the constituent units derived from a carboxy group-containing (meth)acrylic monomer is preferably 0.1 to 20% by mass with respect to the total mass of the (meth)acrylic copolymer, more preferably 0.5 to 10% by mass, and even more preferably 1 to 6% by mass.

Furthermore, the (meth)acrylic copolymer is preferably able to form a cross-linked structure in terms of improving the aggregation strength of the polymer composition, and including a constituent unit derived from a monomer having the following structure, which generates radicals by photo-excitation, is more preferable in terms of improving the holding power in a case of being used as a polymer composition.

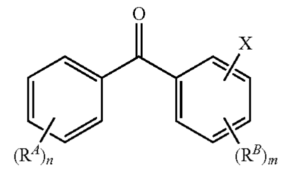

1

(In the formula, $R^A$ and $R^B$ each independently indicate an alkyl group, an alkoxy group, a hydroxyl group, a carboxy group, or a halogen atom, n indicates an integer of 0 to 5, m indicates an integer of 0 to 4, and X indicates a (meth) acryloyloxy group or a (meth)acryloyloxyalkyleneoxy group).

In addition, the weight average molecular weight (Mw) of the (meth)acrylic copolymer, as measured by gel permeation chromatography (GPC), is preferably 5,000 to 2,000,000, more preferably 10,000 to 1,000,000, and even more preferably 30,000 to 350,000. When the Mw is the lower limit value or more, the adhesive layer durability is excellent, and when the Mw is the upper limit value or less, the handling properties (compatibility with other components, coating properties, hot-melt processability, and the like) are excellent.

Furthermore, the glass transition temperature (Tg) of the (meth)acrylic copolymer is preferably 0° C. or lower in terms of the adhesive properties and more preferably −5° C. or lower. Specifically, the glass transition temperature of the polymer is preferably −100° C. or higher and 0° C. or lower and more preferably −80° C. or higher and −5° C. or lower.

It is possible to manufacture the (meth)acrylic copolymer by a known method using known polymerization initiators. For example, as the polymerization method, it is possible to apply known polymerization methods such as a solution polymerization method, a suspension polymerization method, a bulk polymerization method, an emulsion polymerization method, and the like and the solution polymerization method is preferable.

The polymer composition of the present invention may be a mixture of the compound of the present invention with the adhesive polymer, or a mixture of the polymer of the present invention with a compound.

In the polymer composition, the ratio (mass ratio) of the compound to the polymer is preferably in a range of 1:3 to 0.5:99.5 and more preferably 1:9 to 1:70.

The polymer composition of the present invention may further contain other components. It is possible to use known components as other components and examples thereof include solvents, fillers, cross-linking agents, adhesion-giving resins, antioxidants, light stabilizers, metal deactivating agents, anti-ageing agents, moisture absorbents, rust inhibitors, hydrolysis inhibitors, and reaction catalysts.

Examples of antioxidants include phenol-based, phosphorus-based, hydroxylamine-based, and sulfur-based antioxidants.

The polymer composition of the present invention may be used as a liquid adhesive composition including a solvent or used as a hot-melt type adhesive composition including no solvent.

It is possible to use the polymer composition of the present invention as an adhesive cured as necessary with active energy rays. As active energy rays, ultraviolet light is preferable in terms of versatility. Examples of ultraviolet light sources include Xenon lamps, high-pressure mercury lamps, metal halide lamps, and the like.

When the adhesive layer is formed from the polymer composition of the present invention, the melt viscosity when measured at 130° C. and a frequency of 0.02 Hz is preferably 10 to 300 Pa-s and more preferably 20 to 200 Pa-s.

When an adhesive layer is formed from the polymer composition of the present invention, a peel strength (N/25 mm) of 5 to 20 N/25 mm is preferable, and 10 to 17 N/25 mm is more preferable.

When an adhesive layer is formed from the polymer composition of the present invention, attached to a SUS plate, and a load of 1.0 kg is applied with the other end of the adhesive layer down at 40° C., the holding time is preferably 50,000 seconds or more and more preferably 86,400 seconds or more.

When an adhesive layer is formed from the polymer composition of the present invention, attached to a SUS plate, and a load of 1.0 kg is applied with the other end of the adhesive layer down at 80° C., the holding time is preferably 1,500 seconds or more, more preferably 3,000 seconds or more, and even more preferably 20,000 seconds or more.

When the adhesive layer is formed from the polymer composition of the present invention, attached to a SUS plate, and the adhesive layer is peeled off, the glue residue area with respect to the surface area of the SUS plate is preferably 0 area % or more and less than 20 area % and more preferably 0 area %.

<<(Meth)Acrylic Copolymer>>

The (meth)acrylic copolymer of the present invention includes a constituent unit derived from the monomer m having a structure that generates an active species by photoexcitation. The polymer included in the (meth)acrylic copolymer of the present invention has substantially no radical polymerizable group A at the terminal.

As the monomer m, it is possible to use the same monomers m as described above in <<Compound>>.

As the (meth)acrylic copolymer of the present invention, as the constituent units other than the constituent unit derived from the monomer m, it is possible to use the same constituent units as described above in <<Polymer>>.

<Polymer Composition>

It is possible to use the (meth)acrylic copolymer of the present invention including the constituent unit derived from the monomer m as a polymer composition by mixing with a compound having a radical polymerizable group A at the terminal. The aggregation strength of the polymer composition is improved by the formation of a cross-linked structure between the radical polymerizable group A at the terminal of the compound and the structure of the (meth) acrylic copolymer of the present invention, which generates an active species by photoexcitation, in the polymer composition.

<Compound>

The compound included in the polymer composition of the present invention has a radical polymerizable group A at the terminal.

As the compounds, the macromonomers described above are preferable. The macromonomers may or may not include constituent units derived from the monomer m having a structure that generates an active species by photoexcitation.

<<Adhesive Sheet>>

The adhesive sheet of the present invention has an adhesive layer formed using the adhesive composition.

The adhesive sheet may be a sheet formed of only an adhesive layer formed of the adhesive composition of the present invention in sheet form or may be an adhesive sheet in which a peelable substrate is laminated on one surface or both surfaces of an adhesive layer formed of the adhesive composition of the present invention in sheet form.

<Adhesive Layer>

The adhesive layer may be formed of the adhesive composition of the present invention or may be formed of a cured product of the adhesive composition of the present invention. In terms of ease of handling of the adhesive sheet, being formed of an adhesive in which the adhesive composition of the present invention is cured by ultraviolet light is preferable.

It is possible to appropriately set the thickness of the adhesive layer according to the application. For example, 10 to 500 μm is preferable and 20 to 100 μm is more preferable. It is possible to measure the thickness by methods using a constant-pressure thickness measuring device or the like and there are also methods for adjusting from the film thickness of the coater and the solid content of the composition.

Members which are attached using the adhesive composition of the present invention are not particularly limited. For example, use is possible for attaching window-laminating films for vehicles, construction, and the like, attaching labels in labeling displays, attaching various panels such as liquid crystal panels, attaching transparent board materials such as glass, and the like.

EXAMPLES

Hereinafter, a more detailed description will be given of the present invention using Examples, but the present invention is not limited to these Examples. Below, “parts” refers to “parts by mass”. The evaluation was performed by the following method.

<Molecular Weight of Compound Including Two or More Constituent Units Derived from Monomer M>

Measurement was carried out using a gel permeation chromatography (GPC) apparatus (manufactured by Tosoh Corporation, HLC-8320). A 0.2% by mass tetrahydrofuran (THF) solution of the compound was prepared, 10 μL of the solution was charged into the apparatus described above on which columns manufactured by Tosoh Corporation were (TSKgel SuperHZM-MxHZM-MxHZ2000, TSK guard column SuperHZ-L) mounted, and measurement was carried out under conditions of a flow rate of 0.35 mL/min, an eluent of THF (stabilizer: butyl hydroxytoluene (BHT)), and a column temperature of 40° C. The number average molecular weight (Mn) and weight average molecular weight (Mw) were calculated using polystyrene conversion.

<Molecular Weight of Polymer>

Measurement was carried out using a GPC apparatus (manufactured by Tosoh Corporation, HLC-8120). A 0.3% by mass THF solution of the polymer was prepared, 20 μL of the solution was charged into the apparatus described above on which columns manufactured by Tosoh Corporation were (TSKgel SuperHM-Hx4, TSK guard column SuperH-H) mounted, and measurement was carried out under conditions of a flow rate of 0.6 mL/min, an eluent of THF (stabilizer, BHT), and a column temperature of 40° C. The number average molecular weight (Mn) and weight average molecular weight (Mw) were calculated using polystyrene conversion.

<Preparation of Test Pieces>

After diluting the polymer with ethyl acetate such that the composition had a solid content of 33.3%, the compound was added and mixed therein, it was visually confirmed that there was no residue of the dissolved compound, and a polymer composition which was liquid form at room temperature (23° C.) was obtained.

The polymer composition was coated on a PET film with a film thickness of 38 μm using an applicator and dried at 90° C. for 1 hour to form an adhesive layer.

Using a 90 mW high-pressure mercury lamp, a PET film (PET) forming an adhesive layer was irradiated with ultraviolet light in air to cure the adhesive layer. The irradiation energy was 35 mJ/cm$^2$ or 105 mJ/cm$^2$ (actual measured value according to an integrated light intensity meter UV POWER PUCK II (S/N 13685) (manufactured by EIT, USA)). On the upper surface, a peeling-treated PET film (peeling PET) was overlaid and a laminate with a configuration of peeling PET—adhesive layer—PET was obtained. The thickness of the adhesive layer was 50 μm. The laminate after curing was cut into strips 25 mm wide and 250 mm long and used as test pieces.

<Melt Viscosity>

The polymer composition was coated using an applicator and the adhesive layer, which was dried at 90° C. for 1 hour, was measured using a viscoelasticity measuring apparatus HAAKE MARS. The viscosity (η*) value when measured at 130° C. and a frequency of 0.02 Hz using a 35 mm diameter cone plate was set as the melt viscosity value at 130° C.

<Adhesive Strength>

The adhesive layer was exposed by peeling off the peeling PET from the test piece, attached to a 30 mm×110 mm stainless steel (SUS) plate using a 3 kg hand roller such that the attachment surface was 25 mm×70 mm, and the peel strength (N/25 mm) with respect to the SUS plate was measured at a peeling angle of 180° and a tensile speed of 300 mm/min and used as the adhesive strength.

<Holding Power>

At one end of the test piece, the peeling PET was peeled off to expose the adhesive layer and attached horizontally to a 30 mm×110 mm SUS plate using a 3 kg hand roller such that the attachment surface was 25×25 mm. The result was left in a constant temperature and humidity chamber testing device at a temperature of 40° C. or 80° C. and 35% humidity for 15 minutes. Immediately after, a SUS plate was placed such that a force was applied with respect to the attachment surfaces in the shear direction, a load of 1.0 kg was applied with the other end of the test piece down, and the holding time was measured and set as the holding power.

<Substrate Contamination Resistance>

The adhesive layer was exposed by peeling off the peeling PET from the test piece and attached to a 30 mm×110 mm SUS plate using a 3 kg hand roller such that the attachment surface was 25 mm×70 mm. Thereafter, the test piece was peeled off under the same conditions as for the adhesive strength evaluation method, the SUS surface was visually observed, and the substrate contamination resistance was determined according to the following criteria.

A: No glue residue (the ratio of the adhesive residue area to the surface area of the SUS plate is 0 area %).

B: Ratio of glue residue area is more than 0 area % and less than 30 area %.

C: Ratio of glue residue area is 30 area % or more.

The presence or absence of glue residue was checked visually.

Production Example 1 [Dispersant 1]

900 parts of deionized water, 60 parts of sodium 2-sulfoethyl methacrylate, 10 parts of potassium methacrylate, and 12 parts of methyl methacrylate (MMA) were added to a polymerization apparatus provided with a stirrer, a cooling tube, a thermometer, and a nitrogen gas inlet tube and stirred and the temperature was raised to 50° C. while the inside of the polymerization apparatus was substituted with nitrogen. Furthermore, 0.08 parts of 2,2'-azobis(2-methylpropionamidine) dihydrochloride were added as a polymerization initiator and the temperature was raised to 60° C. After the temperature was raised, MMA was continuously added dropwise at a rate of 0.24 parts/min for 75 minutes using a drop pump. After holding the mixture at 60° C. for 6 hours, the mixture was cooled to room temperature to obtain a dispersant 1 with a solid content of 10% by mass.

Production Example 2 [Chain Transfer Agent 1]

1.00 g of cobalt (II) acetate tetrahydrate, 1.93 g of diphenylglyoxime, and 80 mL of diethyl ether previously deoxygenated by nitrogen bubbling, were added to a synthesis apparatus provided with a stirring apparatus under a nitrogen atmosphere and stirred at room temperature for 30 minutes. Furthermore, 10 mL of a boron trifluoride diethyl ether complex was added and stirred for 6 hours. The mixture was filtered and the solid was washed with diethyl ether and vacuum dried for 15 hours to obtain 2.12 g of a chain transfer agent 1, which was a red-brown solid.

Production Example 3 [Compound M-1]

145 parts of deionized water, 0.1 parts of sodium sulfate, and 0.25 parts of the dispersant 1 (solid content 10% by mass) were added to a polymerization apparatus provided with a stirrer, a cooling tube, a thermometer, and a nitrogen gas inlet tube and stirred to form a uniform aqueous solution. Furthermore, 100 parts of MMA, 0.0022 parts of the chain transfer agent 1, and 0.4 parts of Perocta (registered trademark) O (1,1,3,3-tetramethylbutylperoxy 2-ethylhexanoate, manufactured by NOF Corporation) as a polymerization initiator were added to form an aqueous suspension.

Furthermore, the inside of the polymerization apparatus was substituted with nitrogen, the temperature was raised to 80° C. and stirred for 3.5 hours, and, to further increase the polymerization rate, the temperature was raised to 90° C. and held for 1 hour. Thereafter, the mixture was cooled to 40° C. to obtain an aqueous suspension including the compound. The obtained aqueous suspension was filtered with a filter and the residue remaining on the filter was washed with deionized water, dehydrated, and dried at 40° C. for 16 hours to obtain a compound M-1. Table 1 shows the results of molecular weight measurement.

Production Examples 4 to 10 [Compounds M-2 to M-8]

Compounds M-2 to M-8 were produced in the same manner as in Production Example 3, except that the blends were changed as described in Table 1. The units for the blends shown in Table 1 are parts by mass.

TABLE 1

| | | | Production Example | | | | | | | |
|---|---|---|---|---|---|---|---|---|---|---|
| | | | 3 | 4 | 5 | 6 | 7 | 8 | 9 | 10 |
| | Compound | | M-1 | M-2 | M-3 | M-4 | M-5 | M-6 | M-7 | M-8 |
| Blend (parts by mass) | Monomer a1 | MMA | 100 | 90 | 0.01 | 40 | 50 | 50 | 80 | 60 |
| | Monomer a2 | IBXMA | 0 | 0 | 89.98 | 49.99 | 44.99 | 48.99 | 0 | 0 |
| | Monomer a3 | IBMA | 0 | 0 | 0.01 | 0.01 | 0.01 | 0.01 | 0 | 0 |
| | Monomer m1 | 4-MBP | 0 | 10 | 10 | 10 | 0 | 0 | 20 | 40 |
| | Monomer m2 | BPOEMA | 0 | 0 | 0 | 0 | 5 | 1 | 0 | 0 |
| | Initiator | Perocta O | 0.4 | 0.4 | 0.6 | 0.6 | 0.6 | 0.6 | 0.4 | 0.4 |
| | Dispersant 1 | | 0.25 | 0.524 | 0.524 | 0.524 | 0.524 | 0.524 | 0.524 | 0.524 |
| | Chain transfer agent 1 | | 0.0022 | 0.0022 | 0.009 | 0.009 | 0.009 | 0.009 | 0.0022 | 0.0022 |
| Molecular weight | Number average molecular weight Mn | | 3000 | 3000 | 2800 | 1900 | 2600 | 1800 | 4300 | 6000 |
| | Weight average molecular weight Mw | | 5800 | 6800 | 7900 | 3700 | 6100 | 3600 | 10400 | 13100 |

Production Example 11 [(Meth)Acrylic Copolymer A-1]

40 parts of ethyl acetate and 7.7 parts of isopropyl alcohol (IPA) were added to a four-necked flask provided with a stirring apparatus, a thermometer, a cooling tube, and a nitrogen gas inlet port and the external temperature was raised to 85° C. under nitrogen gas ventilation. After the external temperature reached 85° C. and the internal temperature stabilized, a mixture formed of 25 parts of ethyl acetate, 95 parts of n-butyl acrylate (n-BA), 5 parts of acrylic acid (AA), and 0.13 parts of Nyper (registered trademark) BMT-K40 (manufactured by NOF Corporation, trade name) was added dropwise over 4 hours. After finishing the dropwise addition and holding for 1 hour, a mixture formed of 0.5 parts of Perocta-O and 10 parts of ethyl acetate was added over 30 minutes. Thereafter, after holding for 2 hours, 0.5 parts of an antioxidant (manufactured by BASF, trade name Irganox (registered trademark) 1010) was introduced and ethyl acetate was added such that the solid content (ratio of the monomer charge-in amount in (monomer+solvent charge-in amount)) was 53% by mass, then the result was cooled to room temperature to obtain a copolymer solution A-1 including the (meth)acrylic copolymer A-1.

TABLE 2

| Production Example | | | 11 | 12 | 13 |
|---|---|---|---|---|---|
| (Meth)acrylic copolymer A | | | A-1 | A-2 | A-3 |
| Blend (parts by mass) | Compound | M-1 | 0 | 5 | 0 |
| | Monomer | n-BA | 95 | 91.9 | 94.74 |
| | | AA | 5 | 3 | 5.14 |
| | | m1 | 0 | 0.10 | 0.12 |
| Properties | Tg (° C.) | | −40.4 | −37.4 | −40.11 |
| | Mw | | 112000 | 112000 | 157000 |
| | Mn | | 18200 | 18000 | 19000 |
| | Mw/Mn | | 6.2 | 6.2 | 8.2 |

Production Examples 12 and 13

A copolymer solution A-2 including a (meth)acrylic copolymer A-2 and a copolymer solution A-3 including a (meth) acrylic copolymer A-3 were obtained in the same manner as in Production Example 11, except that the compositions were changed as described in Table 2.

Examples 1 to 16, Comparative Examples 1 to 3

Using the polymer compositions obtained by blending the polymers and compounds as described in Tables 3 and 4, test pieces were produced by the method described above and the adhesive strength, holding power, and substrate contamination resistance were evaluated. The evaluation results are shown in Tables 3 and 4. The symbols in each table are as follows.

MMA: Methyl methacrylate
IBXMA: Isobornyl methacrylate
IBMA: Isobutyl methacrylate
IPA: Isopropyl alcohol
n-BA: n-Butyl acrylate
AA: Acrylic acid
m1: 4-methacryloyloxybenzophenone
m2: 4-[2-(methacryloyloxy)ethoxy]benzophenone The polymer compositions of Examples 1 to 16 were confirmed to be superior to the polymer compositions of Comparative Examples 1 to 3 in terms of adhesive strength, holding power, and contamination resistance.

Since Comparative Example 1 was not blended with the compound of the present invention, the adhesive strength, holding power, and substrate contamination resistance were insufficient.

Since Comparative Example 2 was blended only with a monomer having a structure that generates an active species by photoexcitation, the adhesive strength and holding power were insufficient.

Since Comparative Example 3 was blended with a compound having a radical polymerizable group A at the terminal but without having a constituent unit derived from a monomer having a structure that generates an active species by photoexcitation, the holding power and substrate contamination resistance were insufficient.

TABLE 3

| | | | Example 1 | Example 2 | Example 3 | Example 4 | Example 5 | Example 6 |
|---|---|---|---|---|---|---|---|---|
| Blending amount | Polymer | Type | A-1 | | | | A-2 | |
| | | Mass (g) | 8.0 | 7.0 | 9.0 | 7.0 | 9.0 | 8.7 |
| | Compound | Type | M-3 | M-4 | | | | M-1 |
| | | Mass (g) | 0.45 | 0.16 | 0.30 | 0.40 | 0.10 | 0.26 |
| | Ethyl acetate (g) | | 6.1 | 4.7 | 6.0 | 4.9 | 5.8 | 6.0 |
| Polymer composition | Polymer number of parts | | 90.6 | 96.0 | 94.2 | 90.5 | 98.0 | 94.7 |
| | Compound number of parts | | 9.4 | 4.0 | 5.8 | 9.5 | 2.0 | 5.3 |
| | Melt viscosity (Pa-s) | | 42 | 35 | 38 | 41 | 30 | 36 |
| Evaluation results | UV-C integrated light amount (mJ/cm$^2$) | | 105 | | | | | |
| | Adhesive strength (N/25 mm) | | 12.0 | 14.0 | 11.9 | 9.8 | 10.1 | 15.2 |
| | Load 1 kg, 80° C. holding power (s) | | 3574 | 3742 | 86400 < | 86400 < | 86400 < | 63 |
| | Load 1 kg, 40° C. holding power (s) | | 54045 | 86400 < | 86400 < | 86400 < | 86400 < | 40026 |
| | Adhesive residue area | | 0% | 0% | 0% | 0% | 0% | 0% |
| | Adhesive residue | | A | A | A | A | A | A |

| | | | Example 7 | Example 8 | Example 9 | Example 10 | Example 11 |
|---|---|---|---|---|---|---|---|
| Blending amount | Polymer | Type | A-2 | | A-1 | | A-2 |
| | | Mass (g) | 9.0 | 9.0 | 7.0 | 7.0 | 9.0 |
| | Compound | Type | M-2 | | M-4 | | |
| | | Mass (g) | 0.10 | | 0.20 | 0.32 | 0.10 |
| | Ethyl acetate (g) | | 5.8 | | 4.8 | 4.9 | 5.8 |
| Polymer composition | Polymer number of parts | | 98.0 | | 95.0 | 92.2 | 98.0 |
| | Compound number of parts | | 2.0 | | 5.0 | 7.8 | 2.0 |
| | Melt viscosity (Pa-s) | | 33 | | 33 | 37 | 30 |
| Evaluation results | UV-C integrated light amount (mJ/cm$^2$) | | 105 | | 35 | | |
| | Adhesive strength (N/25 mm) | | 10.5 | 14.2 | 13.4 | 12.1 | 11.2 |
| | Load 1 kg, 80° C. holding power (s) | | 86400 < | 1785 | 6630 | 86400 < | 12361 |
| | Load 1 kg, 40° C. holding power (s) | | 86400 < | 86400 < | 86400 < | 86400 < | 86400 < |
| | Adhesive residue area | | 0% | 0% | 0% | 0% | 0% |
| | Adhesive residue | | A | A | A | A | A |

TABLE 4

| | | | Example 12 | Example 13 | Example 14 | Example 15 | Example 16 | Comparative Example 1 | Comparative Example 2 | Comparative Example 3 |
|---|---|---|---|---|---|---|---|---|---|---|
| Blending amount | Polymer | Type | | | A-3 | | | A-1 | A-1 | A-1 |
| | | Mass (g) | 8.3 | 7.2 | 8.9 | 8.7 | 9.0 | 5 | 9 | 8.3 |
| | Compound | Type | M-5 | M-6 | M-7 | | M-8 | — | m1 | M-1 |
| | | Mass (g) | 0.44 | 1.03 | 0.08 | 0.22 | 0.04 | — | 1.00 | 0.50 |
| | Ethyl acetate (g) | | 6.3 | 6.7 | 6.0 | 6.1 | 5.9 | 3.1 | 5.8 | 6.2 |
| Polymer composition | Polymer number of parts | | 91.2 | 79.5 | 98.3 | 95.6 | 99.2 | 100.0 | 100.0 | 90.0 |
| | Compound number of parts | | 8.8 | 20.5 | 1.7 | 4.4 | 0.8 | 0.0 | 0.0 | 10.0 |
| | Melt viscosity (Pa-s) | | 95 | 94 | 99 | 149 | 155 | 32 | 32 | 32 |
| Evaluation results | UV-C integrated light amount (mJ/cm$^2$) | | 35 | 105 | | 35 | | | 105 | |
| | Adhesive strength (N/25 mm) | | 12.3 | 15.5 | 11.2 | 10.0 | 12.8 | 9.4 | 9.6 | 10.5 |
| | Load 1 kg, 80° C. holding power (s) | | 86400 < | 86400 < | 22664 | 86400 < | 86400 < | 2 | 4 | 1 |
| | Load 1 kg, 40° C. holding power (s) | | 86400 < | 86400 < | 86400 < | 86400 < | 86400 < | 27 | 387 | 51 |
| | Adhesive residue area | | 0% | 0% | 0% | 0% | 0% | 90% < | 20% | 90% < |
| | Adhesive residue | | A | A | A | A | A | C | B | C |

INDUSTRIAL APPLICABILITY

The compound of the present invention improves adhesive strength, holding power, and substrate contamination resistance in a case of being used as components of a polymer composition.

What is claimed is:

1. A polymer composition comprising:

a compound comprising: two or more constituent units derived from a monomer M having a radical polymerizable group; and a radical polymerizable group A at a terminal; and a polymer other than the compound, wherein the monomer M includes a monomer m having a structure that generates an active species by photoexcitation, a content of the constituent units derived from the monomer M in the compound is 0.01% by mass or more and 50% by mass or less with respect to a total mass of the compound, and the polymer has a glass transition temperature of 0° C. or lower.

2. The polymer composition according to claim 1, wherein the active species generated by photoexcitation is a radical.

3. The polymer composition according to claim 1, wherein the monomer M has a structure represented by Formula 1,

1

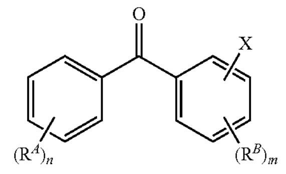

in the formula, $R^A$ and $R^B$ each independently indicate an alkyl group, an alkoxy group, a hydroxyl group, a carboxy group, or a halogen atom, n indicates an integer of 0 to 5, m indicates an integer of 0 to 4, and X indicates a (meth)acryloyloxy group or a (meth) acryloyloxyalkyleneoxy group.

4. The polymer composition according to claim 1, wherein the monomer M includes (meth)acrylate having an alicyclic structure.

5. The polymer composition according to claim 1, wherein a weight average molecular weight of the compound measured by gel permeation chromatography is 1,000 or more and 100,000 or less.

6. The polymer composition according to claim 1, wherein the compound has a structure represented by Formula 2,

2

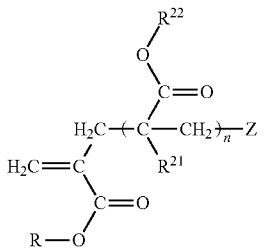

in the formula, R is a group having a structure that generates an active species by photoexcitation, or a linear or branched alkyl group with 1 to 30 carbon atoms, an unsubstituted or substituted group-having alicyclic group, an unsubstituted or substituted group-having aryl group, or an unsubstituted or substituted group-having heterocyclic group, Z is a terminal group, a plurality of $R^{21}$ each independently indicate a hydrogen atom or a methyl group, a plurality of $R^{22}$ each independently indicate a group having a structure that generates an active species by photoexcitation, an unsubstituted or substituted group-having alkyl group, an unsubstituted or substituted group-having alicyclic group, an unsubstituted or substituted group-having aryl group, an unsubstituted or substituted group-having heteroaryl group, an unsubstituted or substituted group-having aralkyl group, an unsubstituted or substituted group-having alkaryl group, an unsubstituted or substituted group-having organosilyl group, or an unsubstituted or substituted group-having (poly)organosiloxane group, the substituted groups in these groups are respectively at least one selected from the group consisting of an alkyl group, an aryl group, a heteroaryl group, a non-aromatic heterocyclic group, an aralkyl group, an alkaryl group, a carboxy group, an alkyloxycarbonylalkyl group, an alkylcarbonyloxyalkyl group, an epoxy group, a hydroxy group, an alkoxy group, a primary amino group, a secondary amino group, a tertiary amino group, an isocyanato group, a sulfonic acid group, and a halogen atom, and n indicates a natural number of 2 or more.

7. The polymer composition according to claim 1, wherein the polymer other than the compound is a (meth) acrylic copolymer.

8. The polymer composition according to claim 7, wherein the (meth)acrylic copolymer includes a constituent unit derived from a monomer represented by Formula 1,

1

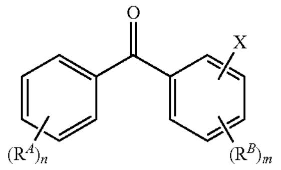

(in the formula, $R^A$ and $R^B$ each independently indicate an alkyl group, an alkoxy group, a hydroxyl group, a carboxy group, or a halogen atom, n indicates an integer of 0 to 5, m indicates an integer of 0 to 4, and X indicates a (meth)acryloyloxy group or a (meth) acryloyloxyalkyleneoxy group).

9. The polymer composition according to claim 1, wherein the compound is a (meth)acrylic copolymer.

10. An adhesive composition comprising:
the polymer composition according to claim 1.

11. An adhesive formed by irradiating the adhesive composition according to claim 10 with ultraviolet light.

12. An adhesive sheet comprising:
an adhesive layer,
wherein the adhesive layer includes the adhesive formed by irradiation with ultraviolet light according to claim 11.

13. An adhesive sheet comprising:
an adhesive layer,
wherein the adhesive layer includes the adhesive composition according to claim 10.

* * * * *